US012508460B2

(12) United States Patent
Teng et al.

(10) Patent No.: US 12,508,460 B2
(45) Date of Patent: Dec. 30, 2025

(54) TRAINING DEVICE AND UTILIZING METHOD THEREOF

(71) Applicant: FREE BIONICS TAIWAN INC., Hsinchu (TW)

(72) Inventors: Ming-Chang Teng, Hsinchu (TW); Yi-Jeng Tsai, Taoyuan (TW); Cheng-Hua Wu, Hsinchu (TW); Kuan-Chun Sun, Hsinchu County (TW)

(73) Assignee: FREE BIONICS TAIWAN INC., Hsinchu (TW)

(*) Notice: Subject to any disclaimer, the term of this patent is extended or adjusted under 35 U.S.C. 154(b) by 806 days.

(21) Appl. No.: 17/809,279

(22) Filed: Jun. 28, 2022

(65) Prior Publication Data

US 2023/0016173 A1 Jan. 19, 2023

Related U.S. Application Data

(60) Provisional application No. 63/221,409, filed on Jul. 13, 2021.

(30) Foreign Application Priority Data

Apr. 29, 2022 (TW) ................................. 111116493

(51) Int. Cl.
*A63B 21/04* (2006.01)
*A61H 1/02* (2006.01)
(Continued)

(52) U.S. Cl.
CPC ........... *A63B 21/0442* (2013.01); *A61H 1/02* (2013.01); *A61H 1/0274* (2013.01);
(Continued)

(58) Field of Classification Search
CPC .......... A63B 21/0442; A63B 21/00181; A63B 21/4017; A63B 21/4011; A63B 2210/02;
(Continued)

(56) References Cited

U.S. PATENT DOCUMENTS 4,237,873 A * 12/1980 Terry ...................... A61F 5/013
602/20
4,669,451 A * 6/1987 Blauth ..................... A61H 1/02
482/901
(Continued)

FOREIGN PATENT DOCUMENTS

CN 109276407 A * 1/2019 ........... A61H 1/0218
CN 111481402 A 8/2020
(Continued)

OTHER PUBLICATIONS

Extended European search report issued by European Patent Office(EPO) dated Dec. 5, 2022 for EP 22182446.9.
(Continued)

*Primary Examiner* — Brandy S Lee
*Assistant Examiner* — Rohan Patel
(74) *Attorney, Agent, or Firm* — WPAT LAW; Anthony King

(57) ABSTRACT

The present disclosure provides a training device and a utilizing method thereof. The training device includes a main assembly and a first attachment assembly. The main assembly includes a housing and a driving component. The driving component is disposed in the housing. The first attachment assembly includes a first rod and a first attachment component. An end of the first rod is connected to the driving component. The driving component drives the first rod to rotate. The first attachment component is disposed on the first rod and attaches to a user.

12 Claims, 19 Drawing Sheets

(51) Int. Cl.
*A63B 23/035* (2006.01)
*A61F 5/042* (2006.01)

(52) U.S. Cl.
CPC .......... *A63B 23/0355* (2013.01); *A61F 5/042* (2013.01); *A61H 2001/0203* (2013.01)

(58) Field of Classification Search
CPC .......... A63B 2220/51; A63B 23/03508; A63B 23/0355; A63B 2024/0093; A63B 2201/1215; A61B 2505/09; B25J 9/0006; A61H 1/0274; A61H 1/0277; A61H 2001/0203
See application file for complete search history.

(56) References Cited

U.S. PATENT DOCUMENTS

| | | | | |
|---|---|---|---|---|
| 4,711,450 | A | 12/1987 | McArthur | |
| 5,255,188 | A * | 10/1993 | Telepko | A61H 1/02 601/40 |
| 5,403,251 | A | 4/1995 | Belsito et al. | |
| 10,220,234 | B2 * | 3/2019 | Marti | A63B 21/4017 |
| 2010/0050765 | A1 * | 3/2010 | Kadota | A61B 5/224 73/379.01 |
| 2012/0040807 | A1 * | 2/2012 | Chen | A63B 21/0004 482/121 |
| 2012/0165158 | A1 * | 6/2012 | Ren | A63B 71/0622 482/7 |
| 2013/0204168 | A1 * | 8/2013 | Bombard | A61H 1/006 601/5 |
| 2020/0129365 | A1 * | 4/2020 | Park | B25J 9/0006 |
| 2021/0162263 | A1 | 6/2021 | Roh | |

FOREIGN PATENT DOCUMENTS

| | | | | |
|---|---|---|---|---|
| CN | 111821143 | A | 10/2020 | |
| CN | 112472523 | A | 3/2021 | |
| EP | 3165208 | A1 | 5/2017 | |
| JP | 2021066970 | A | 4/2021 | |
| KR | 20220008494 | A * | 1/2022 | |
| WO | 2013018205 | A1 | 2/2013 | |
| WO | WO-2020101511 | A1 * | 5/2020 | A61H 1/0281 |

OTHER PUBLICATIONS

Office Action, Cited References and Search Report dated Oct. 18, 2022 issued by the Taiwan Intellectual Property Office(TIPO) for the Taiwan Counterpart Application No. 111116493.
Notice of Reasons for Rejection issued by Japan Patent Office(JPO) dated May 16, 2023 for JP 2022-107134.
Notice of Reasons for Rejection issued by Japan Patent Office(JPO) dated Oct. 31, 2023 for JP 2022-107134.
Decision of Refusal issued by Japan Patent Office(JPO) dated Mar. 19, 2024 for JP 2022-107134.
Office Action issued by China National Intellectual Property Administration(CNIPA) dated Apr. 26, 2024 for CN 202210774211.5.
Office Action issued by China National Intellectual Property Administration(CNIPA) dated Oct. 30, 2024 for CN 202210774211.5.
English Abstract Translation of JP2021066970A.
English Abstract Translation of WO2013018205A1.
English Abstract Translation of CN111821143A.
English Abstract Translation of CN112472523A.
English Translation of Abstract of CN111481402A.
U.S. Pat. No. 10,417,931B2 is the US counterpart of EP3165208A1.

* cited by examiner

TRAINING DEVICE AND UTILIZING METHOD THEREOF

CROSS REFERENCE TO RELATED APPLICATIONS

This application claims priority of Taiwan application No. 111116493 filed on Apr. 29, 2022; U.S. provisional application No. 63/221,409 filed on Jul. 13, 2021, which is incorporated by reference in its entirety.

BACKGROUND

Field of the Invention

The present disclosure relates to a training device and a utilizing method thereof, and more particularly, to a training device for assisting a user and a utilizing method thereof.

Description of Related Art

Conventional training apparatuses have large volumes that may be disadvantageous to users (including both non-disabled users and users with disabilities). Moreover, conventional training apparatuses are mostly passive; that is, the weight of the apparatus itself needs to be used to produce a resistive force in order to achieve the objective of training. However, when a user trains using different weights, the number of training apparatuses increases, leading to inconvenience of the user.

In addition, when a user trains alone using a conventional training apparatus, because such conventional training apparatus lacks the function of feedback assistance, the user may frequently suffer from poor training results or even be injured due to incorrect form. Moreover, conventional training apparatuses cannot provide additional training-related information according to training results for further references for the user.

BRIEF SUMMARY OF THE INVENTION

The present disclosure provides a training device including a main assembly and a first attachment assembly. The main assembly includes a housing and a driving component. The driving component is disposed in the housing. The first attachment assembly includes a first rod and a first attachment component. One end of the first rod is connected to the driving component. The driving component drives the first rod to rotate.

The present disclosure further provides a utilizing method of the training device. The method includes detecting, by a driver of the driving component, an external force provided by a user through the first rod; calculating, by a controller of the driving component, based on a gain, according to the detection of the external force, an auxiliary force for driving the first rod; and controlling, by the controller of the driving component, the driver to drive the first rod with the auxiliary force.

BRIEF DESCRIPTION OF THE DRAWINGS

Embodiments of the present disclosure are described in detail with the accompanying drawings to better understand the present disclosure. It should be noted that some features may not be drawn to scale. In fact, sizes of the features may be increased or decreased as needed for a sake of clarity.

DETAILED DESCRIPTION

Figure 1:
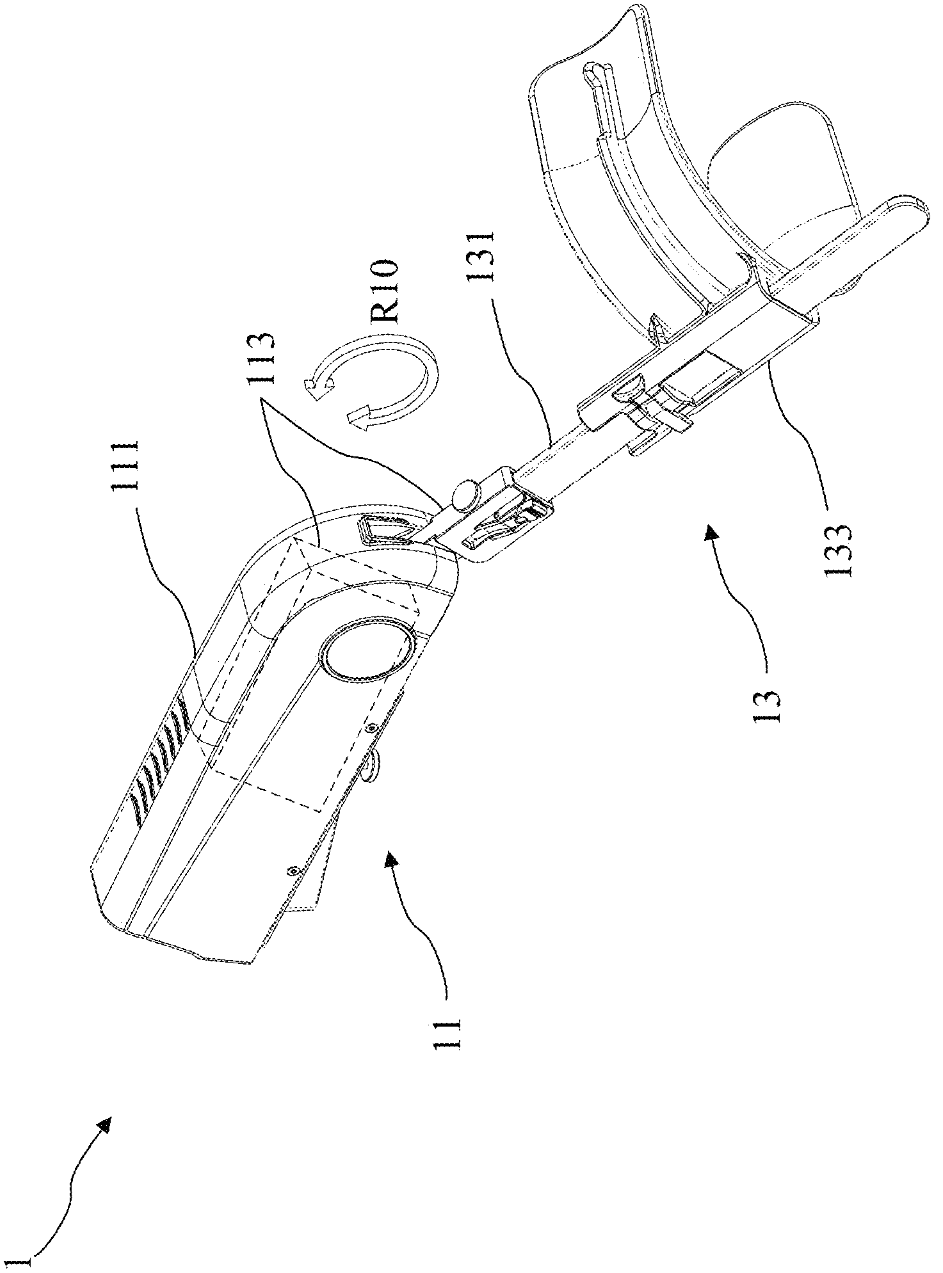
FIG. 1 is a three-dimensional diagram of a training device according to some embodiments of the present disclosure.

To better understand the features, contents, advantages and effects achieved by the present disclosure, the present disclosure is described in detail below by way of embodiments with accompanying drawings. It should be noted that the drawings are used for illustration and assistance purposes for this specification, and ratios and configurations in the drawings are not to be construed as limitations to the scope of the claims of the present disclosure.

The present disclosure provides a training device. A user can mount the training device on various types of carriers, and use the training device to perform various types of training. The present disclosure further provides a utilizing method of the training device. A user can configure the training device to provide auxiliary forces according to different parameters, so as to allow the user to perform various training actions. Moreover, the user can return corresponding training information to a server through the training device, to allow the server to determine training data and corresponding items and provide the training data and the corresponding items to the user.

Please refer to FIG. 1, which is a three-dimensional diagram of a training device 1 according to some embodiments of the present disclosure. Specifically, the training device 1 includes a main assembly 11 and an attachment assembly 13. The main assembly 11 includes a housing 111 and a driving component 113. In some embodiments, the driving component 113 is disposed in the housing 111. In some embodiments, the housing 111 defines an internal accommodating space, and the driving component 113 is disposed partially inside the housing 111 (as shown by dotted lines in FIG. 1). In some embodiments, the housing 111 is in an open form, and the driving component 113 is disposed on the housing 111.

In some embodiments, the attachment assembly 13 includes a rod 131 and an attachment component 133. Specifically, one end of the rod 131 is connected to the driving component 113, and the attachment component 133 is disposed on the rod 131 and is configured to attach to (for example, to be worn by) a user (not shown). When the attachment component 133 is attached to the user, the driving component 113 can be used to drive the rod 131 to rotate (as shown by rotation R10 in FIG. 1). By means of rotating the rod 131 to drive the attachment component 133, the user is provided with an associated auxiliary force (for example, an assisting force in a same direction as, or a resistive force in a direction opposite to, an operating direction of the user), so as to achieve a training effect. In some embodiments, a position at which the attachment component 133 is disposed on the rod 131 is adjustable so as to match a body size of the user.

Figure 2A:
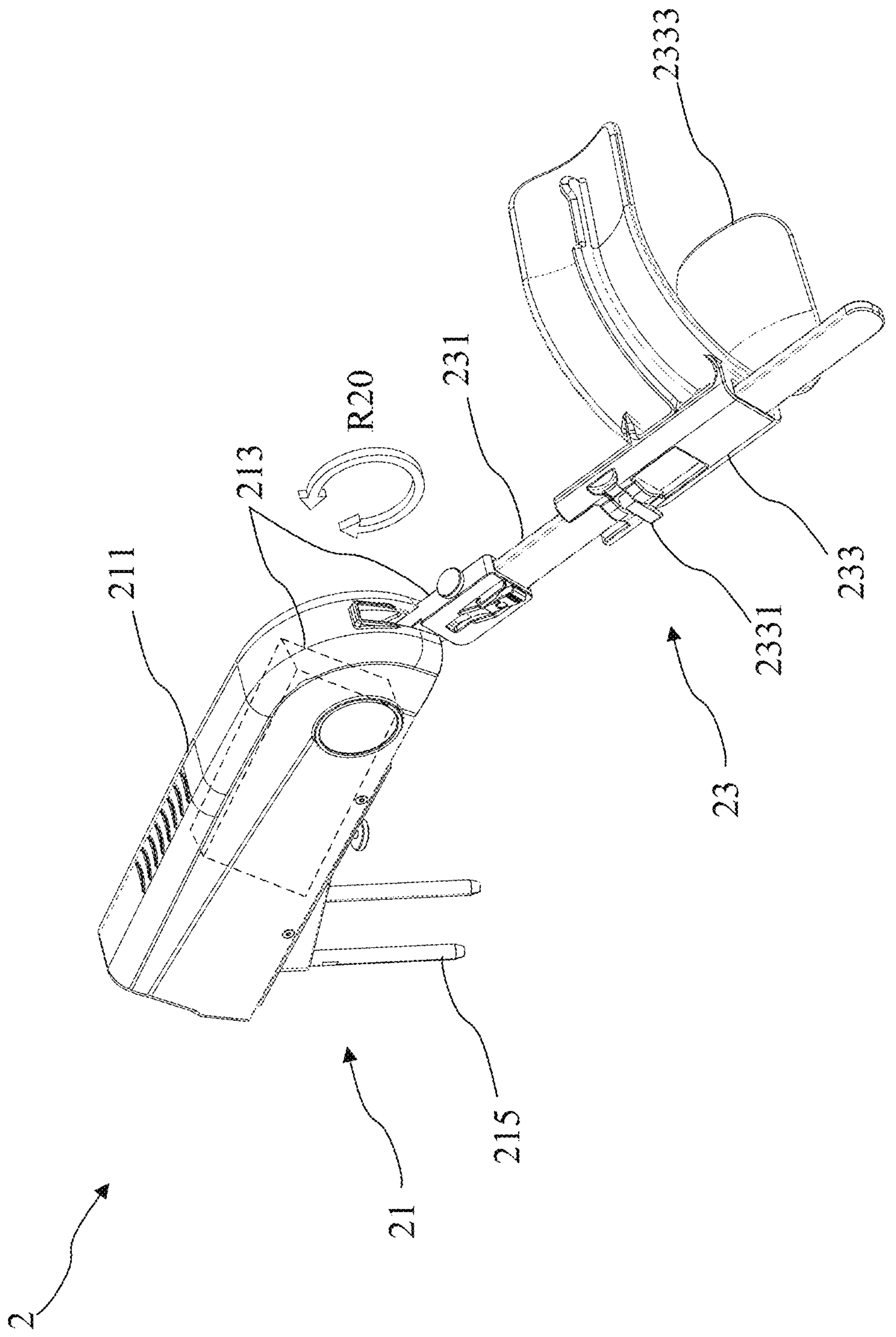
FIG. 2A is a three-dimensional diagram of a training device according to some embodiments of the present disclosure.

Please refer to FIG. 2A, which is a three-dimensional diagram of a training device 2 according to some embodiments of the present disclosure. Specifically, the training device 2 includes a main assembly 21 and an attachment assembly 23. The main assembly 21 includes a housing 211, a driving component 213 and an engaging component 215. In some embodiments, the driving component 213 and the engaging component 215 are disposed in the housing 211. In some embodiments, the housing 211 defines an internal accommodating space, and the driving component 213 is disposed partially inside the housing 211 (as shown by dotted lines in FIG. 2A). In some embodiments, the housing 211 is in an open form, and the driving component 213 is disposed on the housing 211.

In some embodiments, the attachment assembly 23 includes a rod 231 and an attachment component 233. Specifically, one end of the rod 231 is connected to the driving component 213, and the attachment component 233 includes a first fixing unit 2331 and a second fixing unit 2333. The first fixing unit 2331 is used to dispose the attachment component 233 on the rod 231, and the second fixing unit 2333 is used to attach to (for example, to be worn by) a user (not shown). In some embodiments, the first fixing unit 2331 includes a releasable fastening structure used to adjust a position at which the attachment component 233 is disposed on the rod 231, so as to match a body size of the user.

In some embodiments, when the attachment component 233 is attached to a user, the driving component 213 can be used to drive the rod 231 to rotate (as shown by rotation R20 in FIG. 2A). By means of rotating the rod 231 to drive the attachment component 233, the user is provided with an associated auxiliary force (for example, an assisting force in a same direction as, or a resistive force in an opposite direction to, an operating direction of the user), so as to achieve the training effect.

Figure 2B:
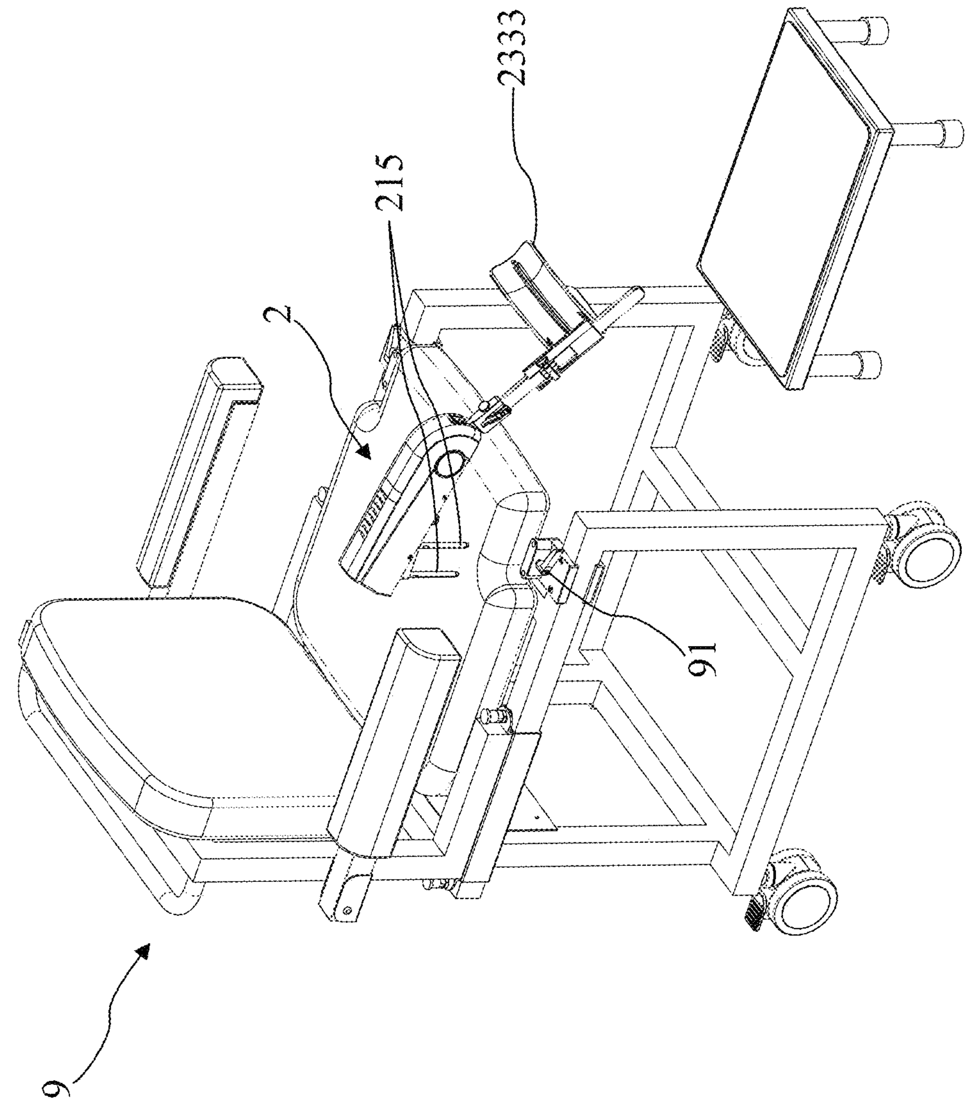
FIG. 2B is a schematic diagram of a training device in use according to some embodiments of the present disclosure.

Please refer to FIG. 2B, which is a schematic diagram of the training device 2 in use according to some embodiments of the present disclosure. Specifically, the engaging component 215 of the main assembly 21 protrudes outward and extends from the housing 211, and is used to engage with an external device 9 (for example, a chair). The external device 9 has a structure for receiving and securing the engaging component 215. When the training device 2 is secured to the external device 9 through the engaging component 215, the user can lean against the external device 9 (for example, sitting on the chair), and the second fixing unit 2333 can be worn on a calf of the user to allow the user to exercise and to operate the training device 2. In some embodiments, the engaging component 215 includes a pin to be inserted into a structure 91 of the external device 9 and to thereby fix the engaging component 215 to the external device 9.

Figure 2C:
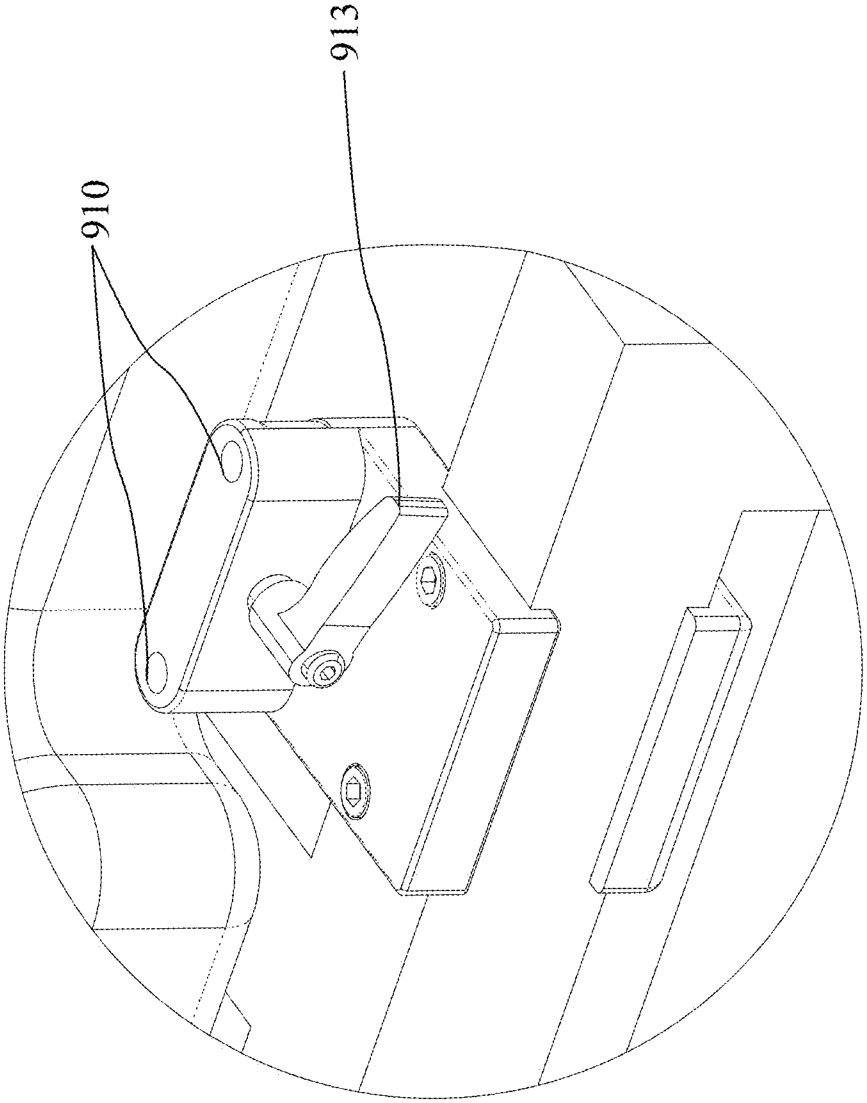
FIG. 2C is an enlarged diagram of an external device according to some embodiments of the present disclosure.

Please refer to FIG. 2C, which is an enlarged diagram of the structure 91 of the external device 9 of the present disclosure. Specifically, the structure 91 includes slots 910 corresponding to the number of pins of the engaging component 215, wherein the slots 910 are configured to receive the engaging component 215. The structure 91 includes a releasable fastening structure 913. When the fastening structure 913 is released, the pins of the engaging component 215 can be inserted into the corresponding slots 910. The fastening structure 913 is then fastened so that the engaging component 215 is fixed in the slot 910.

Figure 2D:
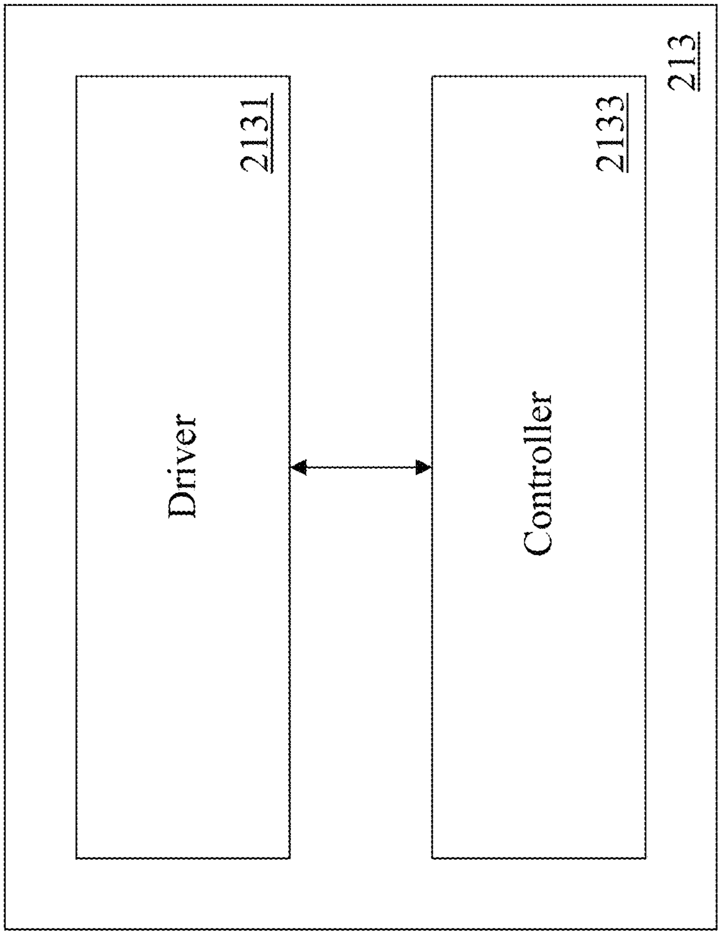
FIG. 2D is a block diagram of a driving component according to some embodiments of the present disclosure.

Please refer to FIG. 2D, which is a block diagram of the driving component 213 according to some embodiments of the present disclosure. Specifically, the driving component 213 includes a driver 2131 and a controller 2133. The driver 2131 is electrically connected to the controller 2133, and electrical signals can be transmitted between the driver 2131 and the controller 2133. The driver 2131 can include a motor, and the controller 2133 can include a micro control unit (MCU) used to control the motor of the driver 2131. Further, the driver 2131 is used to provide an auxiliary force so as to drive the rod 231. The controller 2133 is used to control at least one of a strength, a time period and an operating range of the auxiliary force provided by the driver 2131.

In some embodiments, the driver 2131 can detect an external force applied by a user through the rod 231, that is, the force by which the user operates the training device 2. Based on the detected external force, the controller 2133 can calculate the required auxiliary force based on a gain and control the driver 2131 to drive the rod 231 with the auxiliary force.

In some embodiments, the training device 2 can provide several different training modes. The controller 2133 can calculate the required auxiliary force based on different training modes, and can control the driver 2131 to provide the required auxiliary force to the user. The training device 2 can provide an isokinetic mode, an isotonic mode or an isometric mode.

In some embodiments, when the training device 2 provides the isokinetic mode, the driver 2131 detects an operating speed produced when the user operates the rod 231. The controller 2133 determines whether the operating speed exceeds a threshold. When the operating speed exceeds the threshold, the controller 2133 controls the driver 2131 to dynamically adjust the strength of the auxiliary force, so that the operating speed does not become greater than the threshold.

In some embodiments, when the training device 2 provides the isotonic mode, the controller 2133 controls the driver 2131 to provide a fixed auxiliary force to the user.

In some embodiments, when the training device 2 provides the isometric mode, the controller 2133 locks the driver 2131, such that the strength of the auxiliary force provided by the driver 2131 cancels the external force generated by the user operating the rod 231.

In some embodiments, the driver 2131 detects a rotation amount produced when the rod 231 is operated. When the rotation amount exceeds a predetermined operating range, the controller 2133 controls the driver 2131 to stop operating.

Figure 3A:
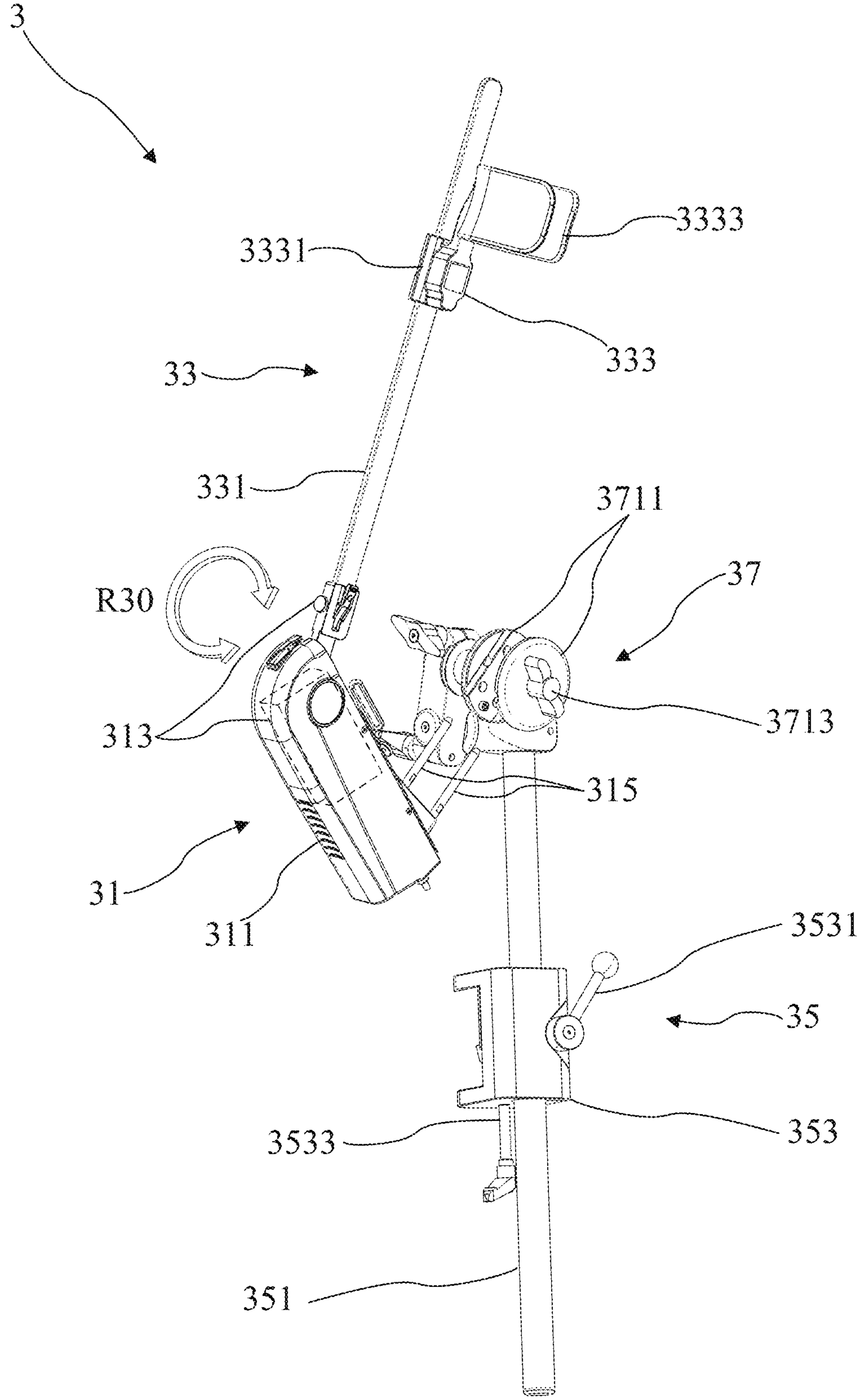
FIG. 3A is a three-dimensional diagram of a training device according to some embodiments of the present disclosure.

Please refer to FIG. 3A, which is a three-dimensional diagram of a training device 3 according to some embodiments of the present disclosure. Specifically, the training device 3 includes a main assembly 31, a first attachment assembly 33, a second attachment assembly 35 and a movable component 37. The main assembly 31 includes a housing 311, a driving component 313 and an engaging component 315. The driving component 313 and the engaging component 315 are disposed in the housing 311. In some embodiments, the housing 311 defines an internal accommodating space, and the driving component 313 is disposed partially inside the housing 311 (as shown by dotted lines in FIG. 3A). In some embodiments, the housing 311 is in an open form, and the driving component 313 is disposed on the housing 311.

In some embodiments, the first attachment assembly 33 includes a first rod 331 and a first attachment component 333. Specifically, one end of the first rod 331 is connected to the driving component 313, and the first attachment component 333 includes a first fixing unit 3331 and a second fixing unit 3333. The first fixing unit 3331 is used to dispose the first attachment component 333 on the first rod 331, and the second fixing unit 3333 is used to attach to (for example, to be worn by) a user (not shown). In some embodiments, the first fixing unit 3331 includes a releasable fastening structure used to adjust a position at which the first attachment component 333 is disposed on the first rod 331, so as to match a body size of the user.

In some embodiments, when the first attachment component 333 is attached to a user, the driving component 313 can be used to drive the first rod 331 to rotate (as shown by rotation R30 in FIG. 3A). By means of rotating the first rod 331 to drive the first attachment component 333, the user is provided with an associated auxiliary force (for example, an assisting force in a same direction as, or a resistive force in an opposite direction to, an operating direction of the user), so as to achieve a training effect.

Figure 3B:
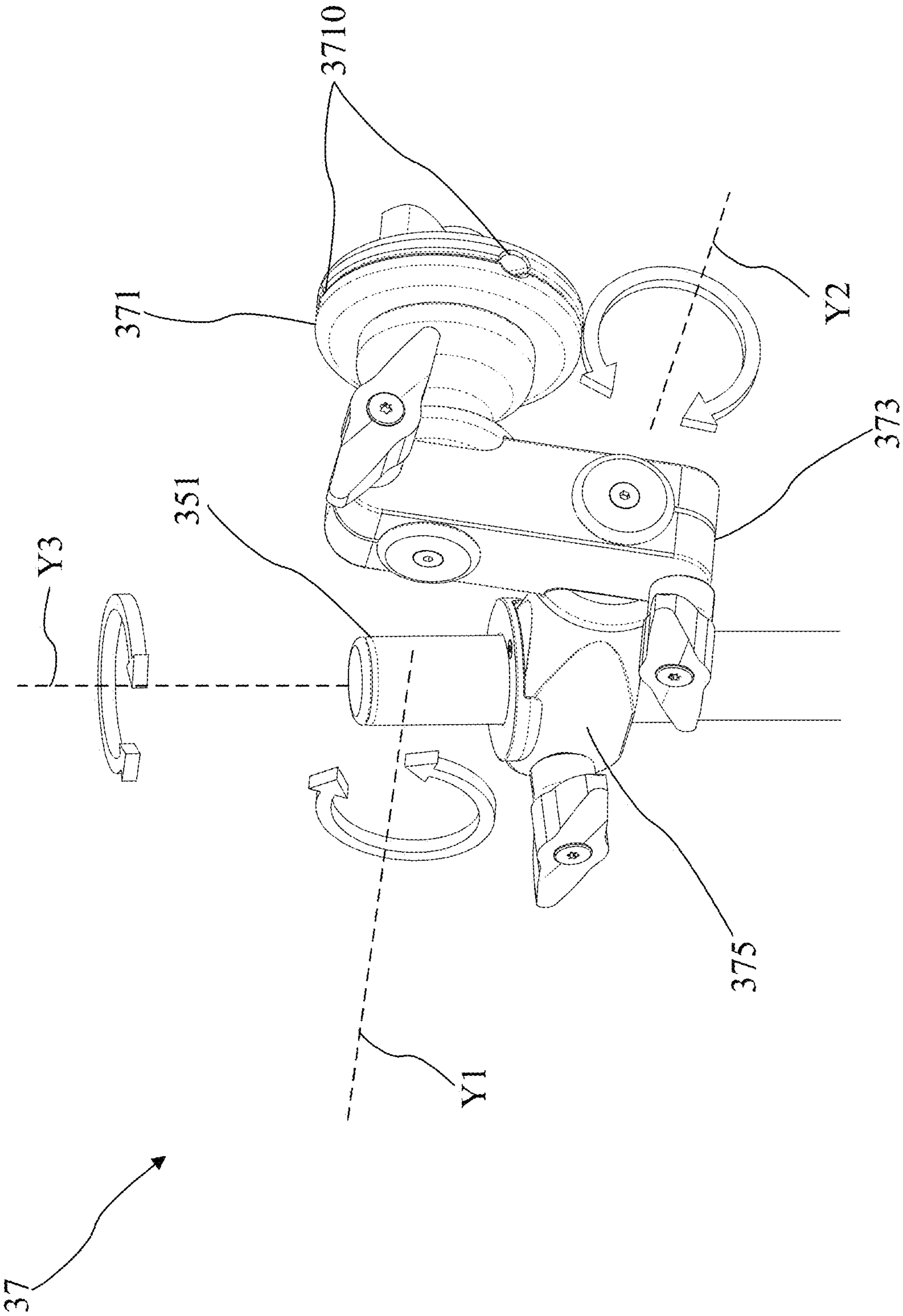
FIG. 3B is an enlarged diagram of a movable component according to some embodiments of the present disclosure.

Please refer to FIG. 3B, which is an enlarged diagram of the movable component 37 of the present disclosure. In some embodiments, the movable component 37 includes a first rotating unit 371 and a second rotating unit 373. Specifically, the first rotating unit 371 is rotatable about a first rotating axis Y1, and the second rotating unit 373 is rotatable about a second rotating axis Y2. In some embodiments, the first rotating axis Y1 is different from the second rotating axis Y2, so as to increase the degree of freedom for operating the training device 3 by the user.

In some embodiments, the engaging component 315 of the main assembly 31 protrudes outward and extends from the housing 311, and is used to engage with the first rotating unit 371. The first rotating unit 371 has a slot 3710 for receiving and fixing the engaging component 315. In some embodiments, the engaging component 315 includes a pin to be inserted into and fixed in the slot 3710 of the first rotating unit 371.

In some embodiments, the first rotating unit 371 includes two clamping pieces 3711 and a turn button 3713. When the two clamping pieces 3711 are joined, a groove formed thereon defines the slot 3710. The turn button 3713 is used to adjust a joining tightness of the two clamping pieces 3711. For example, when the turn button 3713 is rotated clockwise (or counterclockwise), the joining level of the two clamping pieces 3711 is looser, and the engaging component 315 can be inserted into the slot 3710 at such time. Next, the turn button 3713 is rotated counterclockwise (or clockwise), and the joining tightness of the two clamping pieces 3711 is increased so as to securely sandwich the engaging component 315 in the slot 3710.

In some embodiments, the second attachment assembly 35 includes a second rod 351 and a second attachment component 353. Specifically, one end of the second rod 351 is connected to the movable component 37, and the second attachment component 353 is disposed on the second rod 351. In some embodiments, the movable component 37 includes a ring structure 375 having an adjustable level of tightness, wherein the ring structure 375 encircles the second rod 351 and is capable of sliding along a length of the second rod 351. With such structure, the position at which the movable component 37 needs to be secured on the second rod 351 is adjustable and the movable component 37 is rotatable about an axis Y3 of the second rod 351.

In some embodiments, the second attachment assembly 353 includes a through hole having an adjustable size, wherein the second attachment assembly 353 encircles the second rod 351 from one end of the second rod 351. The position at which the second attachment component 353 needs to be secured on the second rod 351 is adjustable, and the second attachment component 353 is secured by a fastening device 3531. Thus, the structure can match body sizes of different users.

Figure 3C:
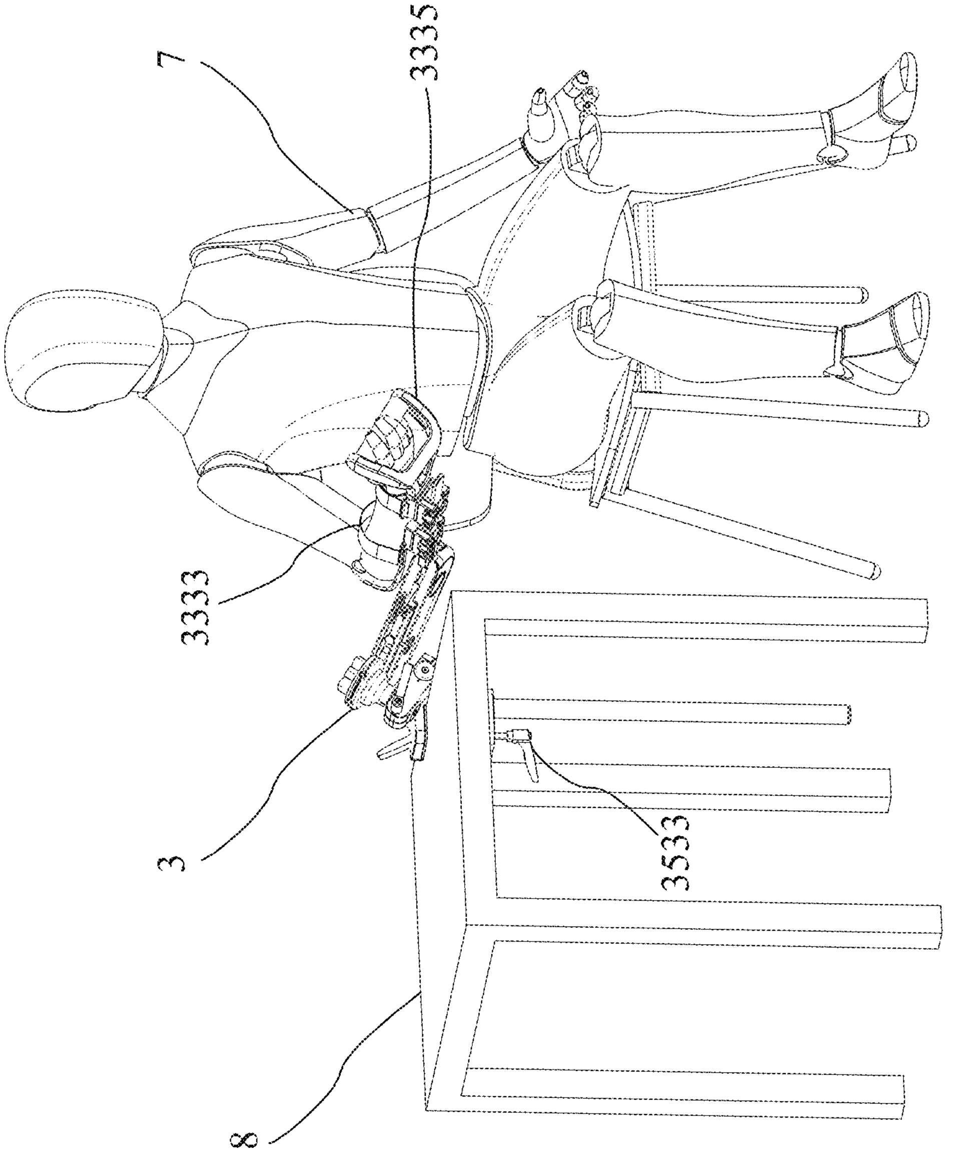
FIGS. 3C and 3D are schematic diagrams of a training device in use according to some embodiments of the present disclosure.
Figure 3D:
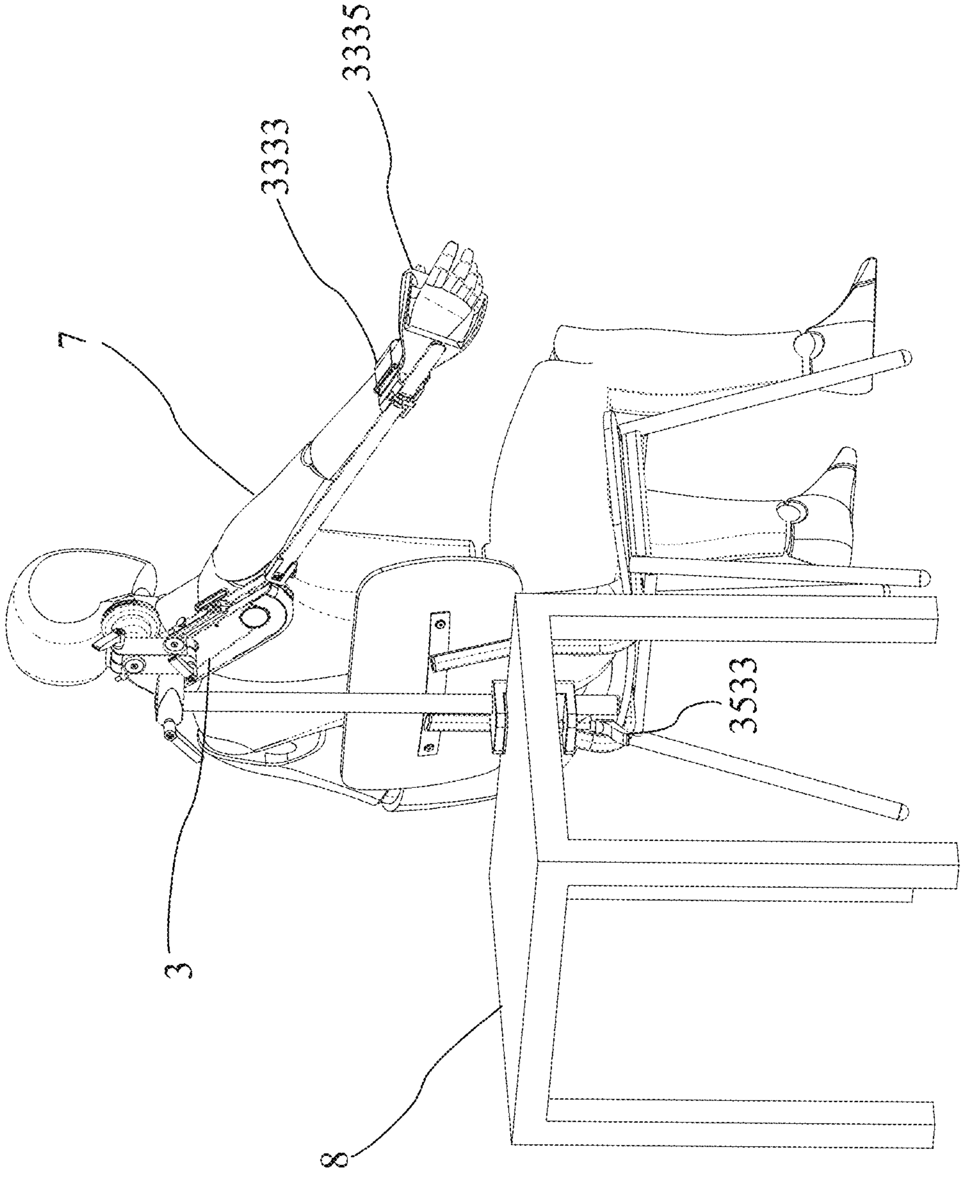
Figure 3E:
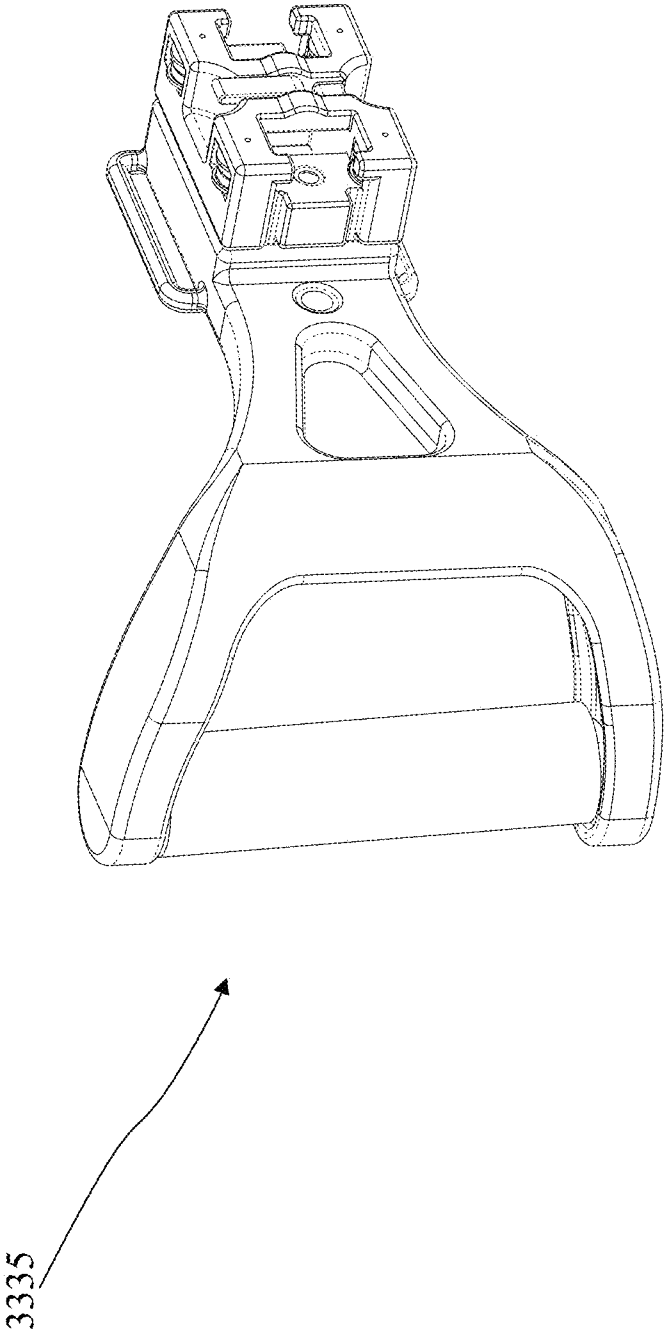
FIG. 3E is a three-dimensional diagram of an accessory of a training device according to some embodiments of the present disclosure.

Please refer to FIGS. 3C, 3D and 3E, wherein FIGS. 3C and 3D show the training device 3 in use according to some embodiments of the present disclosure, and FIG. 3E is a three-dimensional diagram of an accessory 3335 to the training device 3 according to some embodiments of the present disclosure. For example, the second attachment component 353 of the second attachment assembly 35 is used to engage with an external device 8 (for example, a table). In some embodiments, to enhance utilization flexibilities of the training device 3, the second attachment component 353 further includes a clamping component 3533 used to clamp at different positions of the external device 8. When the training device 3 is secured to the external device 8 through the second attachment assembly 35, a user 7 can wear a second fixing unit 3333 (for example, on a forearm) near the external device 8 (for example, sitting on a chair next to the table) so as to operate the training device 3. In some embodiments, in order to allow the user 7 to more conveniently operate the training device 3, an accessory 3335 having a handle can be configured on the first attachment component 333 to facilitate holding and operations of the user 7.

Accordingly, with (1) the configuration of the first rotating unit 371 and the second rotating unit 373 of the movable component 37; (2) the position of the movable component 37 on the second rod 351; (3) the position of the second attachment component 353 on the second rod 351; and (4) the position at which the second attachment component 353 is clamped on the external device 8, the training device 3 is provided with more degree of freedom for operation and thus more effectively matches body sizes of different users.

Figure 3F:
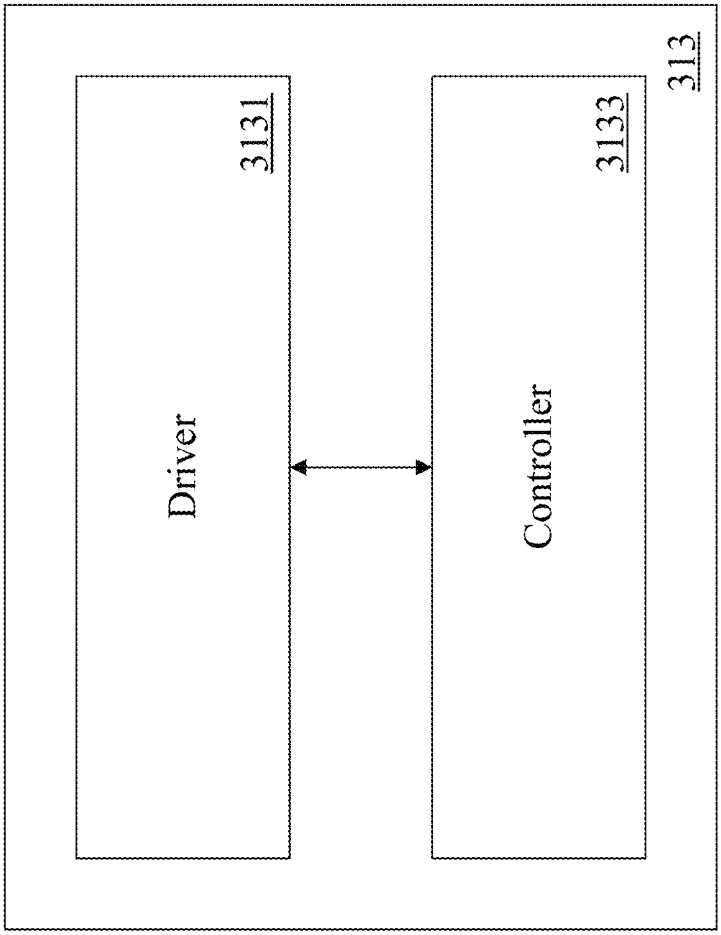
FIG. 3F is a block diagram of a driving component according to some embodiments of the present disclosure.

Please refer to FIG. 3F, which is a block diagram of the driving component 313 according to some embodiments of the present disclosure. Specifically, the driving component 313 includes a driver 3131 and a controller 3133. The driver 3131 can include a motor, and the controller 3133 can include an MCU used to control the motor of the driver 3131. Further, the driver 3131 is used to provide an auxiliary force so as to drive a first rod 331. The controller 3133 is used to control at least one of a strength, a time period and an operating range of the auxiliary force provided by the driver 3131.

In some embodiments, the driver 3131 can detect an external force provided by a user through the first rod 331, that is, the force by which the user operates a training device 3. Based on the detected external force, the controller 3133 can calculate the required auxiliary force based on a gain and can control the driver 3131 to drive the first rod 331 with the auxiliary force.

In some embodiments, the training device 3 can provide different training modes. The controller 3133 can calculate the required auxiliary force based on different training modes, and can control the driver 3131 to provide the auxiliary force to the user. The training device 3 can provide an isokinetic mode, an isotonic mode or an isometric mode.

In some embodiments, when the training device 3 provides the isokinetic mode, the driver 3131 detects an operating speed produced when the user operates the first rod 331. The controller 3133 determines whether the operating speed exceeds a threshold. When the operating speed exceeds the threshold, the controller 3133 controls the driver 3131 to dynamically adjust the strength of the auxiliary force, so that the operating speed does not become greater than the threshold.

In some embodiments, when the training device 3 provides the isotonic mode, the controller 3133 controls the driver 3131 to provide a fixed auxiliary force to the user.

In some embodiments, when the training device 3 provides the isometric mode, the controller 3133 locks the driver 3131, such that the strength of the auxiliary force provided by the driver 3131 cancels the external force generated by the user operating the first rod 331.

In some embodiments, the driver 3131 detects a rotation amount produced when the first rod 331 is operated. When the rotation amount exceeds a predetermined operating range, the controller 3133 controls the driver 3131 to stop operating.

Figure 4A:
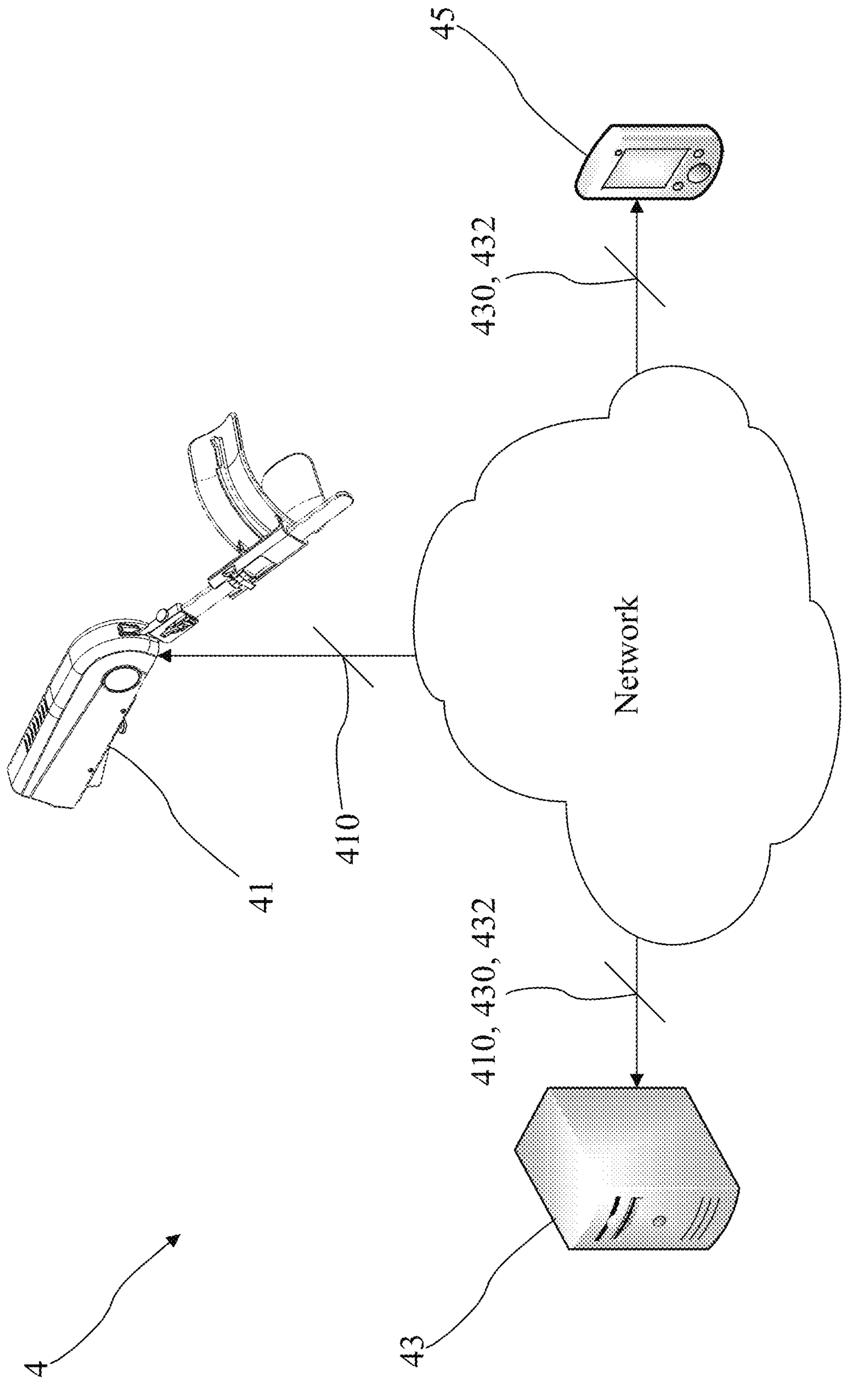
FIG. 4A is a schematic diagram of a training system according to some embodiments of the present disclosure.

Please refer to FIG. 4A, which is a schematic diagram of a training system 4 according to some embodiments of the present disclosure. The training system 4 includes a training device 41 (for example, the training device 1, 2 or 3), a server 43 and a user device 45. When the training device 41 performs the related user operations of the foregoing embodiments, a driver (for example, the driver 2131 or 3131) of the training device 41 can detect operation data 410 of the training device 41 during an operation process. Next, a controller (for example, the controller 2133 or 3133) of the training device 41 can send the operation data 410 to the server 43 through a network using a transmission unit (not shown) of the training device 41.

Next, the server 43 can determine at least one training data 430 based on the operation data 410. Specifically, the operation data 410 can at least include related data such as external force which a user applies to the training device 41, an auxiliary force provided by the training device 41, and an operating range of a rod of the training device 41, and the server 43 can determine, according to the operation data, training data such as (1) whether the user encounters an obstacle while operating the training device 41, (2) whether a training amount of the user is excessive or inadequate, and (3) whether the training form of the user is appropriate. Next, the server 43 can provide the at least one training data 430 to the user device 45 through the network, for the user to determine whether training conditions thereof meet requirements.

It should be noted that, during the process in which the server 43 determines the at least one training data 430 based on the operation data 410, technologies such as big data, artificial intelligence (AI) and machine learning can be used. Specifically, the server 43 can first collect data such as various types of operation data and corresponding training data, and create a determination module based on the data by means of AI and machine learning. Thus, when the server 43 subsequently receives related operation data, the operation data can be input to the determination module to directly acquire the training data.

Figure 4B:
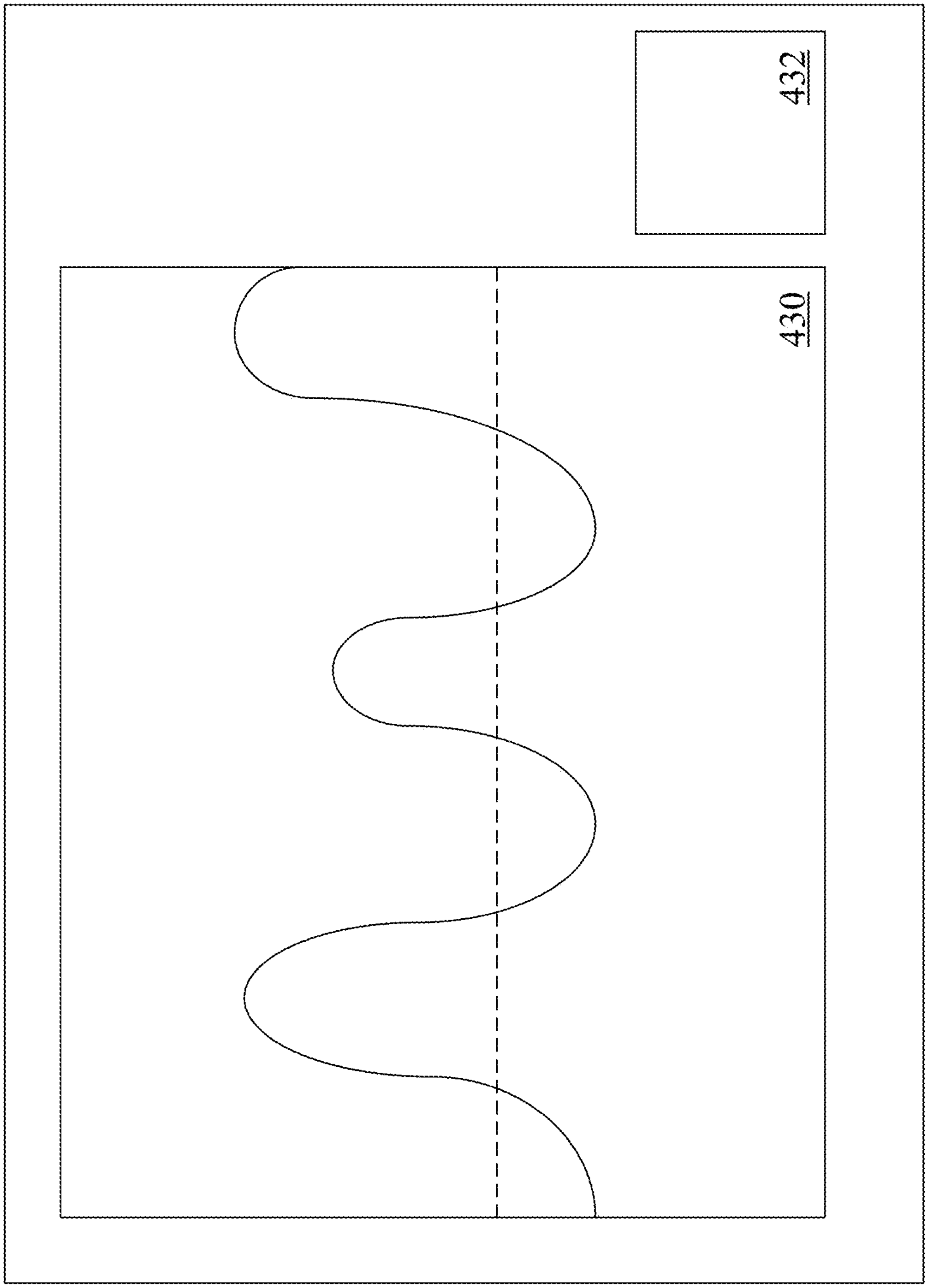
FIG. 4B is a schematic diagram of a graphical user interface according to some embodiments of the present disclosure.

In some embodiments, the server 43 can determine, based on the training data 430, at least one item 432 corresponding to the training data 430, and provide the at least one item 432 to the user device 45 through a network, for the user to refer to the related item 432. For example, when the training data 430 points out that the user may need certain instruction or equipment, the server 43 can determine at least one item 432 (for example, a network link or picture of a course or piece of equipment) satisfying the course or commodity based on the training data 430. Next, the server 43 can provide the at least one item 432 to the user device 45 through a network, and the user device 45 can display the training data 430 and the item 432 on a graphical user interface (for example, the graphical user interface shown in FIG. 4B) using a display unit 451. The item 432 may include a quick response (QR) code.

Figure 5:
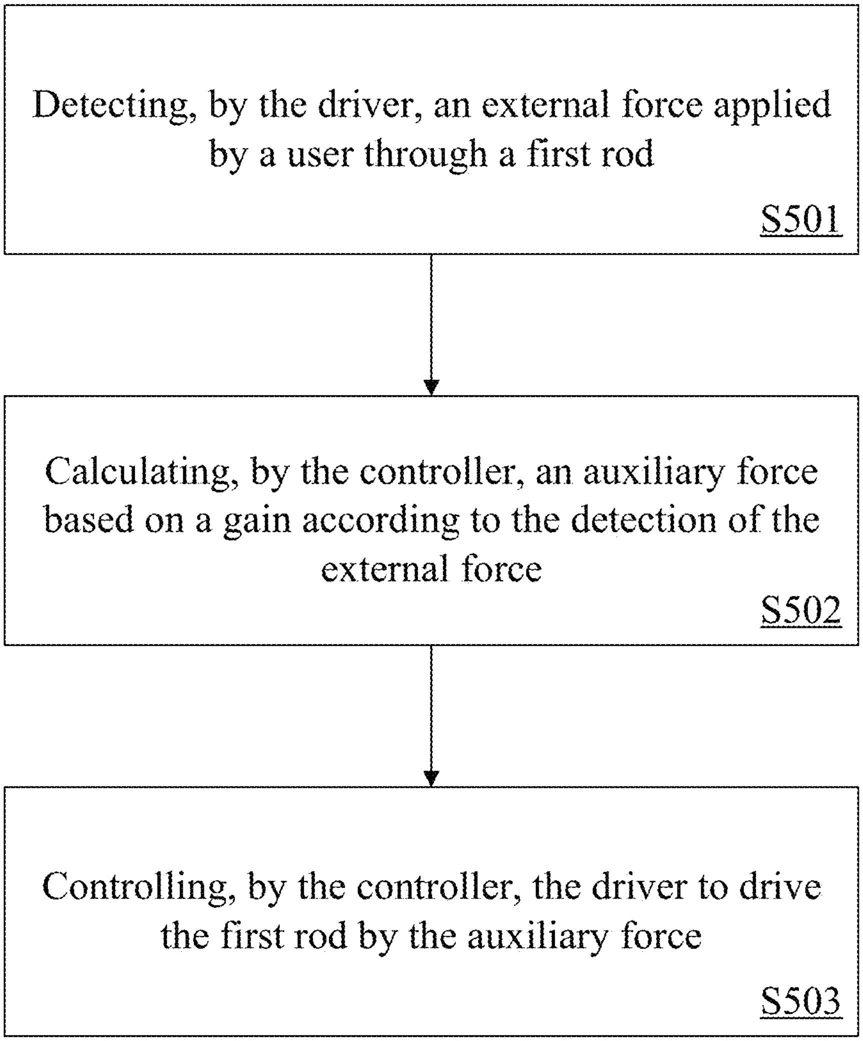
FIG. 5 is a flowchart of a utilizing method of a training device according to some embodiments of the present disclosure.

FIG. 5 shows a flowchart of a utilizing method of a training device (for example, the training devices of the foregoing embodiments) provided according to some embodiments of the present disclosure. Details of the operation of the method are provided below. First, in step S501, a driver of the training device detects an external force applied by a user through a first rod. Next, in step S502, a controller calculates an auxiliary force based on a gain according to the detection of the external force. Next, in step S503, the controller controls the driver to drive the first rod with the auxiliary force.

Figure 6A:
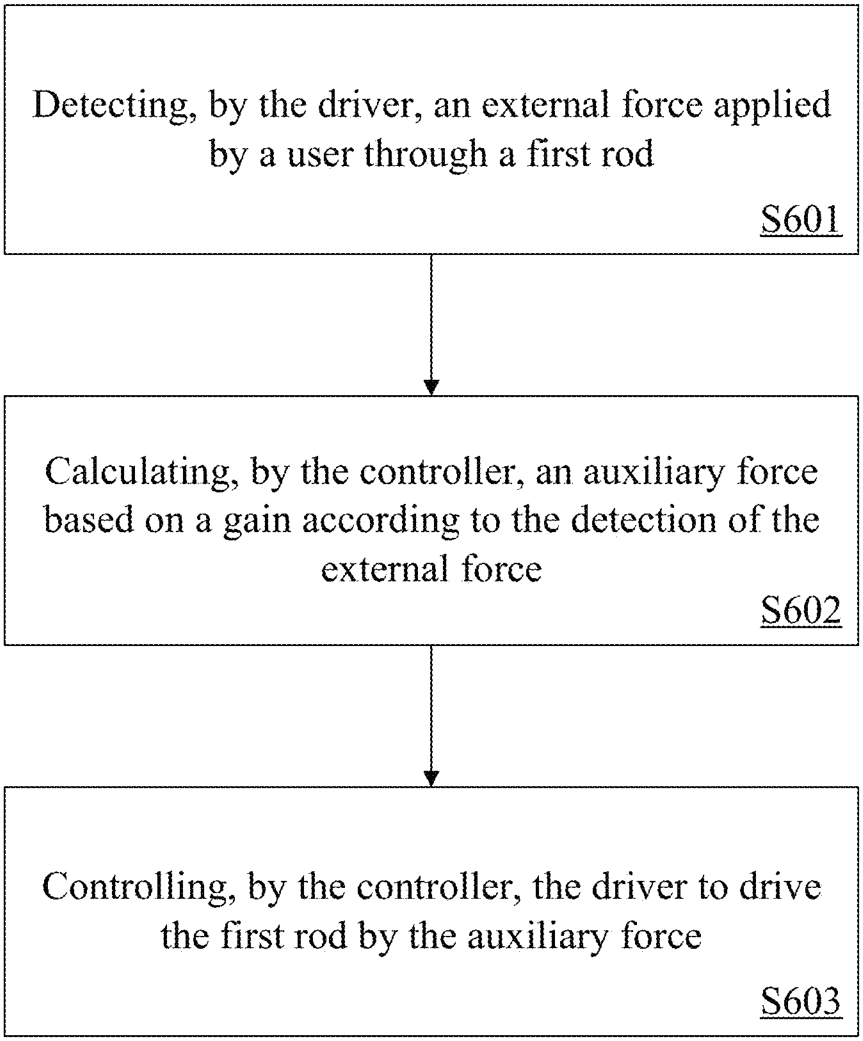
FIGS. 6A to 6C are flowcharts of a utilizing method of a training device according to some embodiments of the present disclosure.
Figure 6B:
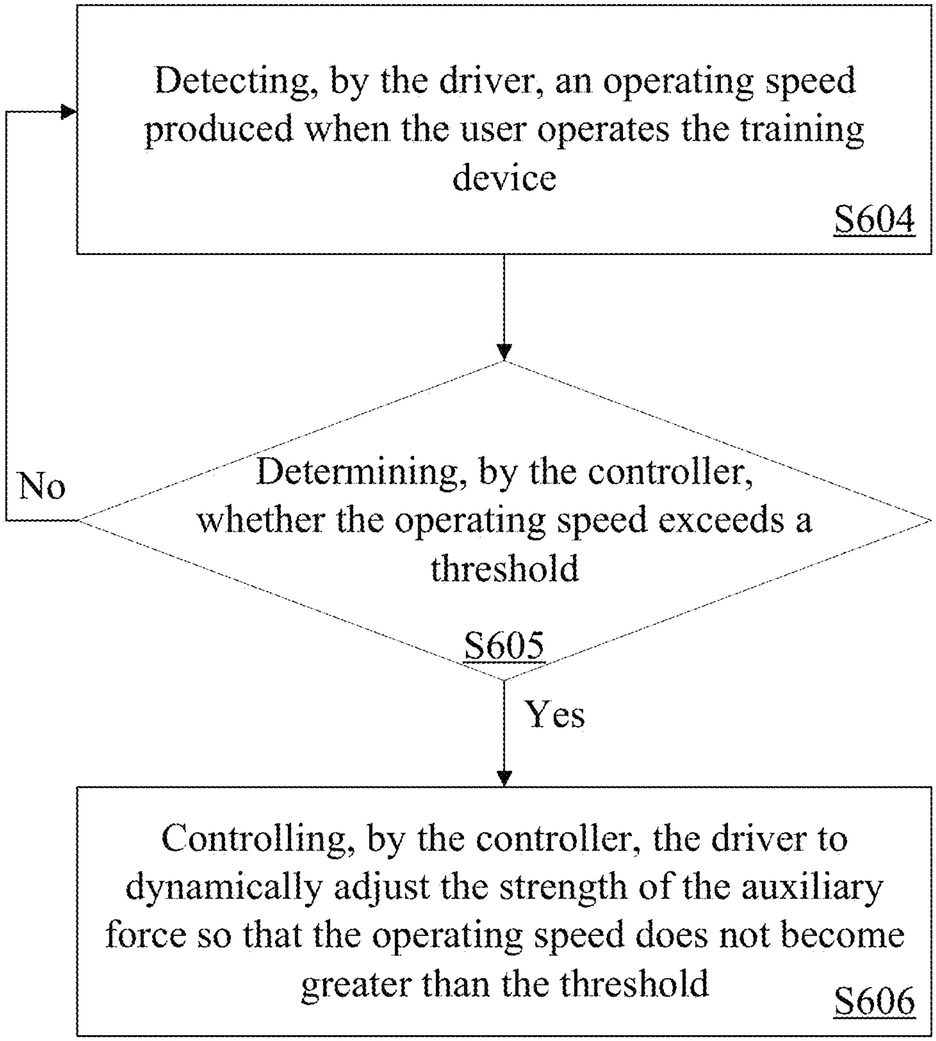
Figure 6C:
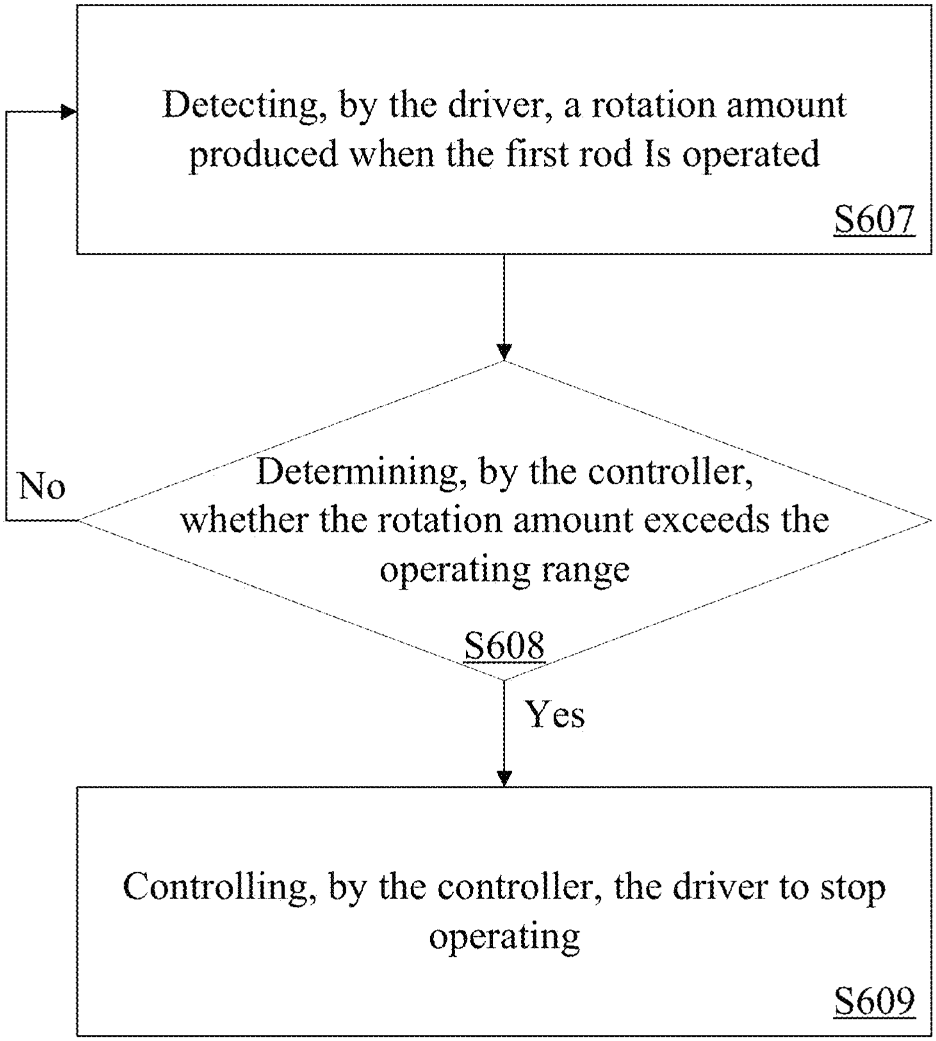

FIGS. 6A to 6C are flowcharts of a utilizing method of a training device (for example, the training devices of the foregoing embodiments) provided according to some embodiments of the present disclosure. Details of the operation of the method are provided below.

First, in step S601, a driver of the training device detects an external force applied by a user through a first rod. In step S602, a controller calculates an auxiliary force based on a gain according to the detection of the external force. In step S603, the controller controls the driver to drive the first rod with the auxiliary force. It should be noted that, in some embodiments, the training device can provide different training modes. The controller can calculate the auxiliary force based on different training modes, and can control the driver to provide the auxiliary force to a user. The training device can provide an isokinetic mode, an isotonic mode or an isometric mode.

In some embodiments, when the training device provides the isokinetic mode, step S604 is further performed, in which the driver detects an operating speed produced when the user operates the training device. Next, in step S605, the controller determines whether the operating speed exceeds a threshold. When the operating speed exceeds the threshold, step S606 is performed, in which the controller controls the driver to dynamically adjust the strength of the auxiliary force, so that the operating speed does not become greater than the threshold. Step S604 is repeated when the operating speed does not exceed the threshold.

In some embodiments, when the training device provides the isotonic mode, step S603 further includes the controller controlling the driver to provide a fixed auxiliary force to the user.

In some embodiments, when the training device provides the isometric mode, step S603 further includes the controller locking the driver, such that the strength of the auxiliary force provided by the driver cancels the external force generated by the user.

In some embodiments, the utilizing method further includes a step of detecting an operating range. Specifically, step S607 is performed, in which the driver detects a rotation amount produced when the first rod is operated. Next, in step S608, the controller determines whether the rotation amount exceeds the operating range. If the rotation amount exceeds the operating range, step S609 is performed, in which the controller controls the driver to stop operating. If the rotation amount does not exceed the operating range, step S607 is repeated.

Figure 7A:
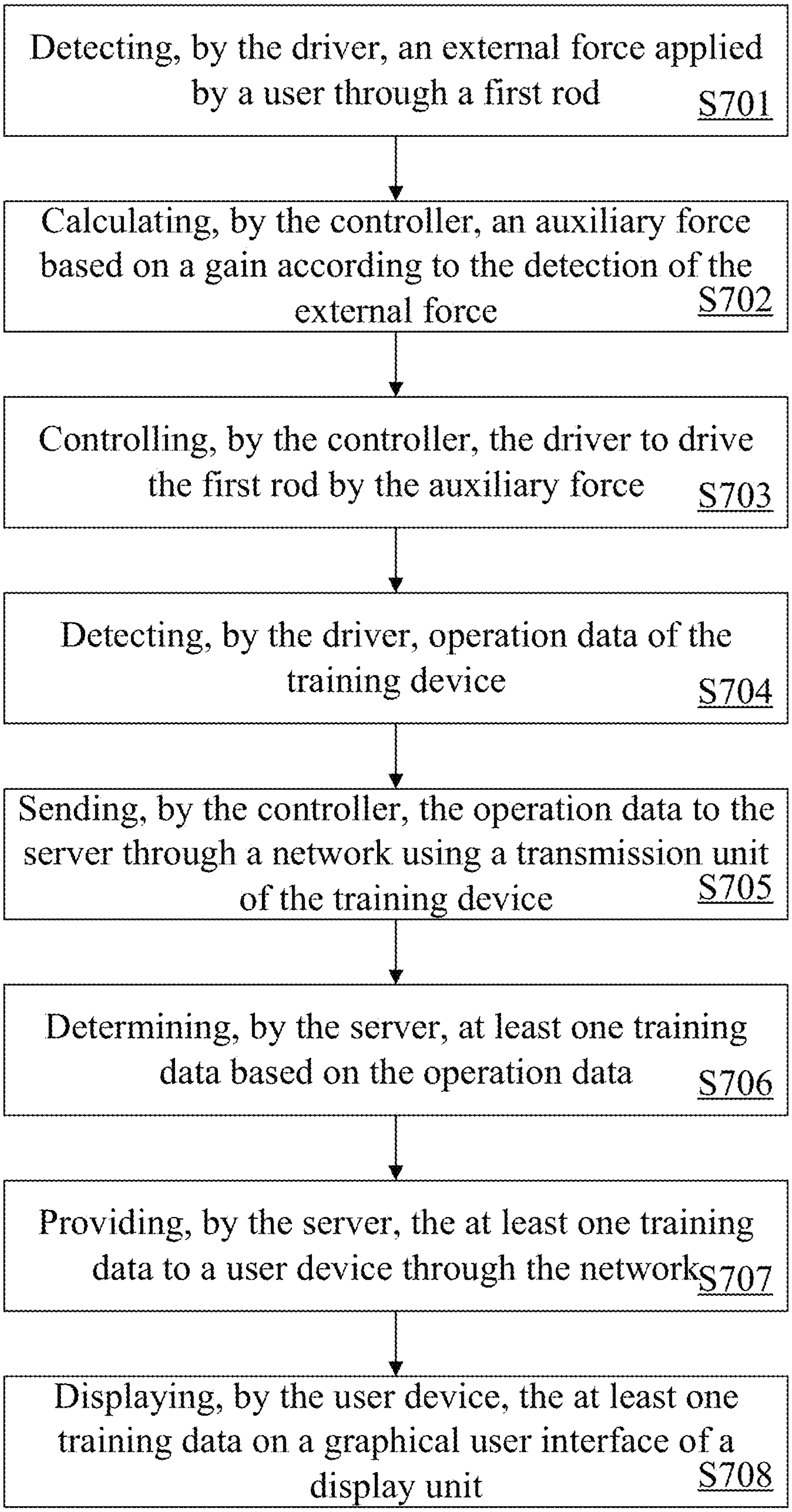
FIGS. 7A and 7B are flowcharts of a utilizing method of a training device according to some embodiments of the present disclosure.
Figure 7B:
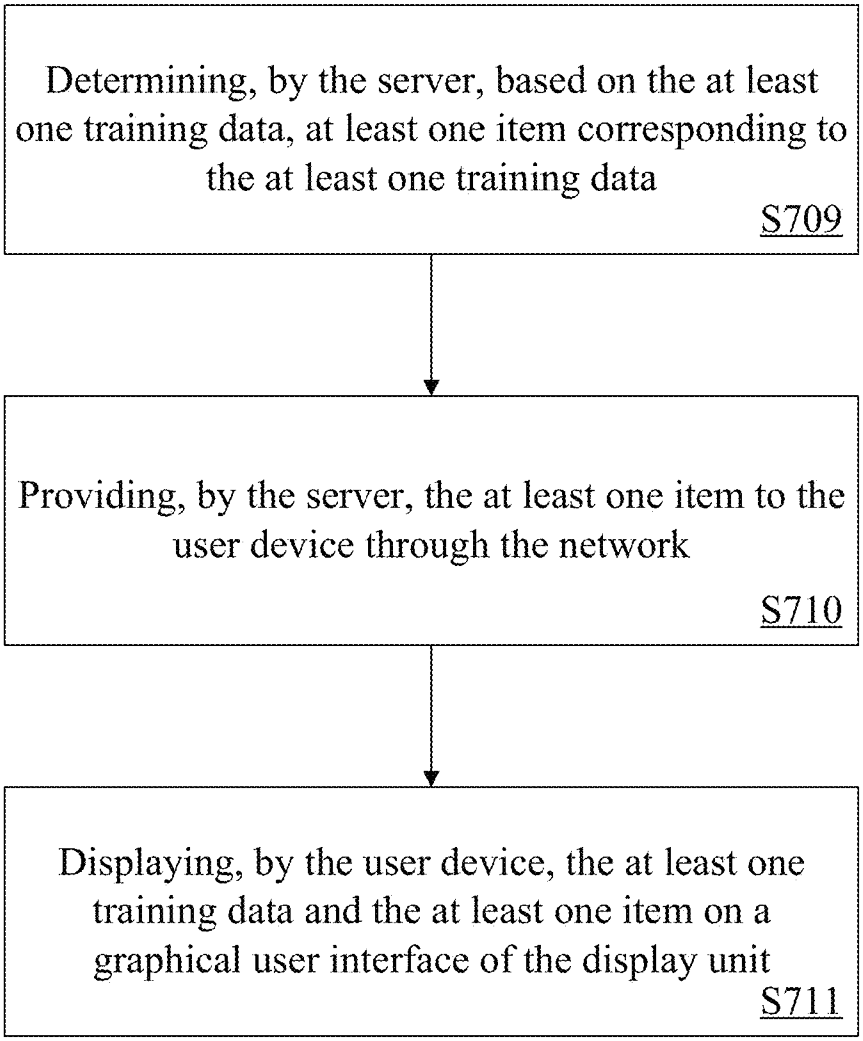

FIGS. 7A and 7B are flowcharts of a utilizing method of a training device (for example, the training devices of the foregoing embodiments) provided according to some embodiments of the present disclosure. Details of the operation of the method are provided below.

First, in step S701, a driver of the training device detects an external force applied by a user through a first rod. In step S702, a controller calculates an auxiliary force based on a gain according to the detection of the external force. In step S703, the controller controls the driver to drive the first rod with the auxiliary force.

In step S704, the driver detects operation data of the training device. In step S705, the controller sends the operation data to the server through a network using a transmission unit of the training device. In step S706, the server determines at least one training data based on the operation data. In step S707, the server provides the at least one training data to a user device through a network. In step S708, the user device displays the at least one training data on a graphical user interface of a display unit.

In some embodiments, step S709 can be selectively performed after step S706. In step S709, the server determines, based on the at least one training data, at least one item corresponding to the at least one training data. In step S710, the server provides the at least one item to the user device through a network. In step S711, the user device display, the at least one training data and the at least one item on a graphical user interface of a display unit. The at least one item includes a QR code.

While this specification contains many specific implementation details, these should not be construed as limitations on the scope of any features or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

The subject invention has been described with reference to embodiments and particular applications with the understanding that features of the subject invention may be practiced individually and/or in various combinations and/or on various types of exercise equipment. Also, persons skilled in the art will recognize that various modifications may be made to the embodiments, in any of its applications, without departing from the scope of the subject invention. Furthermore, alternative embodiments may be made with different component materials, structures, and/or spatial relationships, and nonetheless fall within the scope of the present invention. In view of the foregoing, the subject invention should be limited only to the extent of allowable claims that issue from this application or any related application.

The terminology used in the description of the present disclosure is for the purpose of describing particular embodiments only, and is not intended to limit the disclosure. As used in the description of the disclosure and the appended claims, the singular forms "a," "an" and "the" are intended to include the plural forms as well, unless the context clearly indicates otherwise. It will also be understood that the term "and/or" as used herein refers to and encompasses any and all possible combinations of one or more of the associated listed items.

It shall be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof. The use of directional adjectives "above," "under," "upper," "lower," "below," "left," "right," "up," "down," "top," "bottom," "vertical," "horizontal," and like terms, are meant to assist with understanding relative relationships among design elements and should not be construed as meaning an absolute direction in space nor regarded as limiting. For example, in some embodiments, "a first component is on a second component" describes the first component being on the second component (the first component is directly on the second component), some other components between the first and second components.

Terms such as "approximately," "substantially," or "about" are applied to describe a small variation of a structural unit of an apparatus. When a term is used in conjunction with another term to describe a particular characteristic of the claimed disclosure, such term can indicate the exact events or circumstances, and similar exact events or circumstances.

Obviously, numerous modifications and variations of the present disclosure are possible in light of the above teachings. It is therefore to be understood that within the scope of the appended claims, the present disclosure may be practiced otherwise than as specifically described herein.

What is claimed is:

1. A training device, comprising:

a main assembly, comprising:
- a housing;
- an engaging component, comprising a pin disposed on the housing; and
- a driving component, disposed in the housing; and a first attachment assembly, comprising:
- a first rod, one end of the first rod being connected to the driving component, wherein the driving component drives the first rod to rotate; and
- a first attachment component, disposed on the first rod, comprising:
  - a first fixing unit, comprising a releasable fastening structure configured to dispose the first attachment component on the first rod; and a second fixing unit, configured to attach to a user, a second attachment assembly, comprising:

a second rod; and a second attachment component, disposed on the second rod, and configured to attach to an external device; and a movable component, comprising:

a first rotating unit, rotating about a first rotating axis, and comprising a slot for receiving the pin of the engaging component;

a second rotating unit, connected to the first rotating unit and rotating about a second rotating axis, wherein the first rotating axis is different from the second rotating axis; and a ring structure, having an adjustable level of tightness, connected to the second rotating unit and encircling the second rod, wherein the slot is defined by a groove formed by joining two clamping pieces of the first rotating unit, and the movable component is rotatable about an axis of the second rod through the ring structure, wherein the driving component comprises:

a driver, configured to detect an external force applied by the user through the first rod, and provide an auxiliary force for driving the first rod; and a controller, configured to control at least one of a strength, a time period and an operating range of the auxiliary force provided by the driver according to the external force, wherein the auxiliary force is an assisting force in the same direction as the external force or a resistive force in an opposite direction to the external force.

2. The training device according to claim 1, wherein the second attachment component further comprises a clamping component configured to clamp the external device.

3. A utilizing method of the training device according to claim 1, comprising:

detecting, by the driver, the external force applied by the user through the first rod;

calculating, by the controller, the auxiliary force based on a gain according to the detection of the external force; and controlling, by the controller, the driver to drive the first rod with the auxiliary force.

4. The utilizing method according to claim 3, further comprising:

detecting, by the driver, an operating speed produced when the first rod is operated; and when the operating speed exceeds a threshold, controlling, by the controller, the driver to dynamically adjust the strength of the auxiliary force so that the operating speed does not become greater than the threshold.

5. The utilizing method according to claim 3, wherein the strength of the auxiliary force is constant.

6. The utilizing method according to claim 3, wherein the controlling, by the controller, the driver to drive the first rod with the auxiliary force further comprises:

controlling, by the controller, the driver to drive the first rod with the auxiliary force within the time period.

7. The utilizing method according to claim 3, further comprising:

detecting, by the driver, a rotation amount provided when the first rod is operating; and when the rotation amount exceeds the operating range, controlling, by the controller, the driver to stop operating.

8. The utilizing method according to claim 3, further comprising:

detecting, by the driver, operation data of the training device; and sending, by the controller, the operation data to a server through a network using a transmission unit of the training device.

9. The utilizing method according to claim 8, further comprising:

determining, by the server, at least one training data based on the operation data; and providing, by the server, the at least one training data to a user device through the network.

10. The utilizing method according to claim 9, further comprising:

determining, by the server, based on the at least one training data, at least one item corresponding to the at least one training data; and providing, by the server, the at least one item to the user device through the network.

11. The utilizing method according to claim 10, further comprising:

displaying, by the user device, the at least one training data and the at least one item on a graphical user interface of a display unit.

12. The utilizing method according to claim 11, wherein the at least one item comprises a quick response (QR) code.

* * * * *